(12) United States Patent
Jeong et al.

(10) Patent No.: US 10,040,741 B2
(45) Date of Patent: Aug. 7, 2018

(54) METHOD FOR MANUFACTURING HIGH PURITY GLYCOL BASED COMPOUND

(71) Applicants: Samsung Display Co. Ltd., Yongin-si (KR); ENF TECHNOLOGY CO., LTD., Seoul (KR)

(72) Inventors: Jae Woo Jeong, Suwon-si (KR); Hong Sick Park, Suwon-si (KR); Bong Kyun Kim, Hwaseong-si (KR); Seung Ho Yoon, Hwaseong-si (KR); Sang Dai Lee, Asan-si (KR); Young Jin Park, Asan-si (KR); Hyo Won Park, Asan-si (KR); Sang Moon Yun, Asan-si (KR)

(73) Assignees: Samsung Display Co., Ltd., Yongin-si (KR); ENF TECHNOLOGY CO., LTD., Seoul (KR)

( * ) Notice: Subject to any disclaimer, the term of this patent is extended or adjusted under 35 U.S.C. 154(b) by 501 days.

(21) Appl. No.: 14/865,493

(22) Filed: Sep. 25, 2015

(65) Prior Publication Data

US 2016/0297732 A1    Oct. 13, 2016

(30) Foreign Application Priority Data

Apr. 13, 2015 (KR) ........................ 10-2015-0051908

(51) Int. Cl.
 *C07C 41/42* (2006.01)
 *C07C 41/46* (2006.01)
 *B01D 3/00* (2006.01)

(52) U.S. Cl.
 CPC .............. *C07C 41/42* (2013.01); *B01D 3/009* (2013.01); *C07C 41/46* (2013.01)

(58) Field of Classification Search
 CPC .......... C07C 41/42; C07C 41/46; B01D 3/009
 See application file for complete search history.

(56) References Cited

U.S. PATENT DOCUMENTS 4,060,504 A    11/1977   Higginbottom
2010/0046488 A1    2/2010   Wentink
2011/0112230 A1    5/2011   Cano Sierra et al.

FOREIGN PATENT DOCUMENTS

| KR | 10-2002-0073534 A | 9/2002 |
| KR | 10-2003-0049530 A | 6/2003 |
| KR | 10-0574852 B1 | 4/2006 |
| KR | 10-2011-0053244 A | 5/2011 |
| KR | 10-2011-0109670 A | 6/2011 |
| KR | 10-2012-0135368 A | 12/2012 |
| WO | 2010021948 A1 | 2/2010 |

OTHER PUBLICATIONS

Translation of KR-10-0574852 from K-PION obtained Apr. 3, 2018.*

* cited by examiner

*Primary Examiner* — Jonathan Miller
(74) *Attorney, Agent, or Firm* — H.C. Park & Associates, PLC

(57) ABSTRACT

Provided is a method for manufacturing a glycol based compound. The method comprises agitating a mixture of a first glycol based compound, a hydrazide based compound, and a sulfonic acid based compound, and performing fractional distillation of resultant materials of the agitating to recover a second glycol based compound having a formaldehyde content of 0 ppm.

9 Claims, No Drawings

METHOD FOR MANUFACTURING HIGH PURITY GLYCOL BASED COMPOUND

CLAIM OF PRIORITY

This application makes reference to, incorporates into this specification the entire contents of, and claims all benefits accruing under 35 U.S.C. §119 from an application for METHOD FOR MANUFACTURING HIGH PURITY GLYCOL BASED COMPOUND earlier filed in the Korean Intellectual Property Office on Apr. 13, 2015 and there duly assigned Serial No. 10-2015-0051908.

BACKGROUND OF THE INVENTION

Field of the Invention

The present invention relates to a method for manufacturing a high purity glycol based compound.

Description of the Related Art

In processes of manufacturing a semiconductor and a display such as a TFT-LCD, lithography is widely used to manufacture electronic circuits and pixels.

The lithography is a method that is used to generate a fine pattern on a substrate. That is, the lithography is a process of transferring a circuit pattern of a mask onto a substrate by irradiating the substrate on which photoresist that is a photosensitive material is spread with light through the mask on which a desired pattern is printed, and in respective unit processes, many kinds of chemical processing solutions, such as thinner, stripping agent, cleaning agent, and etching agent. Since a series of lithography processes as described above are mostly performed in an airtight clean zone to protect the above-described components against external pollution, regulations on formaldehyde content in the chemical processing solutions has been strengthened.

Formaldehyde is a material which stimulates a nose and eyes with a pungent odor, and has components harmful to humans and natural environments. Recently, formaldehyde has been suspected to cause cancer, and has become the center of interest all over the world. Further, legal regulations on formaldehyde have been strengthened, and it is demanded not to include formaldehyde in the chemical processing solutions.

Formaldehyde is a material having a low boiling point, and at ambient temperature, it exists in a gaseous state. However, in a glycol organic solvent having polarity, formaldehyde exists in a dissolved state.

In the case of other solvents except for the glycol organic solvent, formaldehyde can be removed through general distillation. However, in the case of the glycol organic solvent, formaldehyde is continuously generated from the glycol organic solvent due to a specific reaction, and thus it is not possible to remove formaldehyde using the general distillation.

SUMMARY OF THE INVENTION

Accordingly, one subject to be solved by the present invention is to provide a method for manufacturing a high purity glycol based compound from which formaldehyde is completely removed.

Additional advantages, subjects, and features of the present invention will be set forth in part in the description which follows and in part will become apparent to those having ordinary skill in the art upon examination of the following or may be learned from practice of the present invention.

In one aspect of the present invention, provided a method for manufacturing a glycol based compound. The method comprises agitating a mixture of a first glycol based compound, a hydrazide based compound, and a sulfonic acid based compound; and performing fractional distillation of resultant materials of the agitating to recover a second glycol based compound having a formaldehyde content of 0 ppm.

The agitating the mixture of the first glycol based compound, the hydrazide based compound, and the sulfonic acid based compound may be performed for 1 to 60 minutes at a temperature of 20° C. to 200° C. while maintaining a hydrogen ion concentration (pH) of 3 to 5.

The performing the fractional distillation of the resultant materials of the agitating may comprise a first distillation process of removing moisture and low boiling point impurities, and a second distillation process of removing high boiling point formaldehyde.

The method may further comprise performing a filtration process of removing fine particles included in the second glycol based compound.

The first glycol based compound may be at least one selected from the group consisting of $C_1$ to $C_6$ alkylene glycols, $C_1$ to $C_6$ alkyl ether based compounds of $C_1$ to $C_6$ alkylene glycols, and $C_1$ to $C_6$ alkyl ether acetate based compounds of $C_1$ to $C_6$ alkylene glycols.

The first glycol based compound may be at least one selected from the group consisting of ethylene glycol, propylene glycol, butylenes glycol, ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether, diethylene monoglycol methyl ether, diethylene monoglycol ethyl ether, diethyleneglycol diethyl ether, diethylene glycol monobutylenes ether, diethyleneglycol dibutyl ether, dipropyleneglycol monomethyl ether, dipropyleneglycol dimethyl ether, dipropyleneglycol monobuty ether, dipropyleneglycol dibutyl ether, triethylene glycol monomethyl ether, triethylene glycol dimethyl ether, triethylene glycol monoethyl ether, triethylene glycol diethyl ether, triethyleneglycol monobutyl ether, and triethyleneglycol dibutyl ether, ethylene glycol methyl ether acetate, ethylene glycol monoethyl ether acetate, ethylene glycol monobutyl ether acetate, and propylene glycol monomethyl ether acetate.

The hydrazide based compound may be at least one selected from the group consisting of acetic hydrazide, octanoate hydrazide, succinic acid dihydrazide, propionic acid hydrazide, benzyl hydrazide, oxalic acid dihydrazide, malic acid dihydrazide, glutaric acid dihydrazide, adipic acid dihydrazide, sebacic acid dihydrazide, maleic dihydrazide, fumaric acide dihydrazide, itaconic acide dihydrazide, carbonic acid dihydrazide, phthalic acid dihydrazide, terephthalic acid dihydrazide, isophtalic acid dihydrazide, 1,2,4-butane tri carbohydrazide, 1,1,4-butane tri carbohydrazide, 1,2,5-pentane tri carbohydrazide, 1,3,6-hexane tri carbohydrazide, 1,3,7-heptane tri carbohydrazide, 1-hydroxy-1,2,4-butane tri carbohydrazide, 3-bromobenzoic acid hydrazide, 4-bromobenzoic acid hydrazide, 2-chlorobenzoic acid hydrazide, 4-chlorobenzoic acid hydrazide, 2-fluorobenzoic acid hydrazide, 3-fluorobenzoic acid hydrazide, 4-fluorobenzoic acid hydrazide, 3-hydroxybenzoic acid hydrazide, salicylic acid hydrazide, 2,4-dihydroxybenzoic acid hydrazide, 2-aminobenzoic acid hydrazide, 4-aminobenzoic acid hydrazide, 2,4-diaminobenzoic acid hydrazide, paratoluic hydrazide, phenylacetic hydrazide, 4-methoxy-benz hydrazide, and 2-hydroxy-4-methoxy benzoic acid hydrazide.

The hydrazide based compound may be added to the first glycol based compound with a content of 0.005 to 1.0 parts by weight with respect to 100 parts by weight of the first glycol based compound.

The sulfonic acid based compound may be at least one selected from the group consisting of an aliphatic sulfonic acid including a methane sulfonic acid and an ethane sulfonic acid; an aromatic sulfonic acid including an o-toluene sulfonic acid, a m-toluene sulfonic acid, a p-toluene sulfonic acid, an o-phenol sulfonic acid, a m-phenol sulfonic acid, a p-phenol sulfonic acid, and a benzene sulfonic acid; and a naphthalene-α-sulfonic acid.

It should be noted that effects of the present invention are not limited to those described above and other effects of the present invention will be apparent to those skilled in the art from the following descriptions.

According to the aspects of the present invention, at least the following effects can be achieved.

The formaldehyde can be completely removed, and thus it is possible to provide a high purity glycol based compound having formaldehyde content of 0 ppm.

The effects according to the present invention are not limited to the contents as exemplified above, but further various effects are included in the description.

DETAILED DESCRIPTION OF THE INVENTION

Features of the inventive concept and methods of accomplishing the same may be understood more readily by reference to the following detailed description of preferred embodiments. The inventive concept may, however, be embodied in many different forms and should not be construed as being limited to the embodiments set forth herein. Rather, these embodiments are provided so that this disclosure will be thorough and complete and will fully convey the concept of the inventive concept to those skilled in the art, and the inventive concept will only be defined by the appended claims.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used in this specification, specify the presence of stated features, integers, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list. Further, the use of "may" when describing embodiments of the present invention refers to "one or more embodiments of the present invention." Also, the term "exemplary" is intended to refer to an example or illustration. As used herein, the terms "use," "using," and "used" may be considered synonymous with the terms "utilize," "utilizing," and "utilized," respectively.

Hereinafter, embodiments of the present invention and comparative examples will be described in detail.

A method for manufacturing a high purity glycol based compound comprises agitating a mixture of a first glycol based compound, a hydrazide based compound, and a sulfonic acid based compound, and performing fractional distillation of resultant material of the agitating, and recovering a second glycol based compound having a formaldehyde content of 0 ppm.

The first glycol based compound means an unrefined glycol based compound as a starting material having the formaldehyde content that exceeds 0 ppm. The second glycol based compound means a refined glycol based compound as the resultant material having the formaldehyde content of 0 ppm.

In an unlimited example, as the first glycol based compound, $C_1$ to $C_6$ alkylene glycols, $C_1$ to $C_6$ alkyl ether based compounds of $C_1$ to $C_6$ alkylene glycols, and $C_1$ to $C_6$ alkyl ether acetate based compounds of $C_1$ to $C_6$ alkylene glycols may be solely or mixedly used.

In an unlimited example, as the $C_1$ to $C_6$ alkylene glycols, ethylene glycol, propylene glycol, and butylenes glycol may be solely or mixedly used.

In an unlimited example, as the $C_1$ to $C_6$ alkyl ether based compounds of the $C_1$ to $C_6$ alkylene glycols, ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether, diethylene monoglycol methyl ether, diethylene monoglycol ethyl ether, diethyleneglycol diethyl ether, diethylene glycol monobutylenes ether, diethyleneglycol dibutyl ether, dipropyleneglycol monomethyl ether, dipropyleneglycol dimethyl ether, dipropyleneglycol monobuty ether, dipropyleneglycol dibutyl ether, triethylene glycol monomethyl ether, triethylene glycol dimethyl ether, triethylene glycol monoethyl ether, triethylene glycol diethyl ether, triethyleneglycol monobutyl ether, and triethyleneglycol dibutyl ether may be solely or mixedly used.

In an unlimited example, as the $C_1$ to $C_6$ alkyl ether acetate based compounds of the $C_1$ to $C_6$ alkylene glycols, ethylene glycol methyl ether acetate, ethylene glycol monoethyl ether acetate, ethylene glycol monobutyl ether acetate, and propylene glycol monomethyl ether acetate may be solely or mixedly used.

In the case of other organic compounds except for the glycol based compound, formaldehyde may be removed through general distillation. However, as shown in Reaction formula 1 below, as the glycol based compound, formaldehyde that is derived from the glycol base compound exists even after the general distillation. Accordingly, in the case of the glycol based compound, it is difficult to completely remove the formaldehyde through general distillation.

[Reaction formula 1]

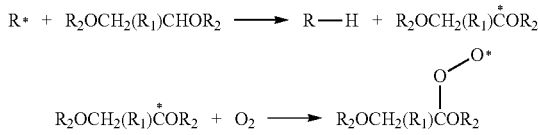

-continued

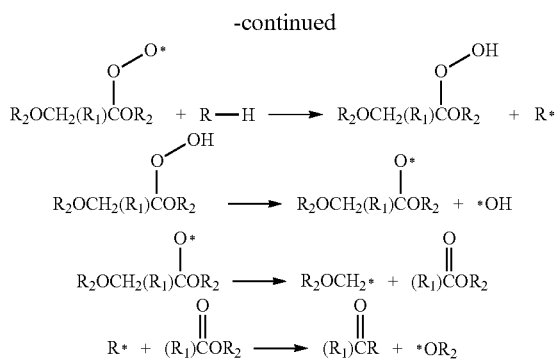

In Reaction formula 1, R may be alkyl radical having hydrogen or carbon the number of which is 1 or more, $R_1$ may be one of hydrogen, a methyl group, and an ethyl group, $R_2$ may be an alkyl group having carbon the number of which is equal to or larger than 1 and equal to or smaller than 10, an alkoxy group having carbon the number of which is equal to or larger than 1 and equal to or smaller than 10, an aryl group, or an alkyl aryl group having carbon the number of which is equal to or larger than 1 and equal to or smaller than 10.

In an embodiment of the present invention, a hydrazide based compound and a sulfonic acid based compound are added to the first glycol based compound, and thus the formaldehyde derived from the first glycol based compound can be completely removed. In addition, a hydrazide based compound and a sulfonic acid based compound are added to organic compounds, and thus formaldehydes derived from the organic compounds can be completely removed.

The hydrazide based compound is a compound that corresponds to a dehydration condensed product material of an amino group of hydrazine and a carboxyl group of carboxyl acid, and may serve as a kind of formaldehyde scavenger by refinement through a chemical reaction with formaldehyde.

The hydrazide based compound may be added to the first glycol based compound with the content of 0.005 to 1.0 parts by weight with respect to 100 parts by weight of the first glycol based compound.

In an unlimited example, as the hydrazide based compound, acetic hydrazide, octanoate hydrazide, succinic acid dihydrazide, propionic acid hydrazide, benzyl hydrazide, oxalic acid dihydrazide, malic acid dihydrazide, glutaric acid dihydrazide, adipic acid dihydrazide, sebacic acid dihydrazide, maleic dihydrazide, fumaric acide dihydrazide, itaconic acide dihydrazide, carbonic acid dihydrazide, phthalic acid dihydrazide, terephthalic acid dihydrazide, isophtalic acid dihydrazide, 1,2,4-butane tri carbohydrazide, 1,1,4-butane tri carbohydrazide, 1,2,5-pentane tri carbohydrazide, 1,3,6-hexane tri carbohydrazide, 1,3,7-heptane tri carbohydrazide, 1-hydroxy-1,2,4-butane tri carbohydrazide, 3-bromobenzoic acid hydrazide, 4-bromobenzoic acid hydrazide, 2-chlorobenzoic acid hydrazide, 4-chlorobenzoic acid hydrazide, 2-fluorobenzoic acid hydrazide, 3-fluorobenzoic acid hydrazide, 4-fluorobenzoic acid hydrazide, 3-hydroxybenzoic acid hydrazide, salicylic acid hydrazide, 2,4-dihydroxybenzoic acid hydrazide, 2-aminobenzoic acid hydrazide, 4-aminobenzoic acid hydrazide, 2,4-diaminobenzoic acid hydrazide, paratoluic hydrazide, phenylacetic hydrazide, 4-methoxy-benz hydrazide, and 2-hydroxy-4-methoxy benzoic acid hydrazide may be solely or mixedly used.

The sulfonic acid based compound is a compound that includes a sulfonic acid group, and expedites a reaction between the hydrazide based compound and the formaldehyde. The sulfonic based compound can maintain hydrogen ion concentration (pH) of a mixture of the first glycol based compound, the hydrazide based compound, and the sulfonic acid based compound in the range of 3 to 5.

In an unlimited example, the sulfonic acid based compound may be an aliphatic sulfonic acid including a methane sulfonic acid and an ethane sulfonic acid; an aromatic sulfonic acid including an o-toluene sulfonic acid, a m-toluene sulfonic acid, a p-toluene sulfonic acid, an o-phenol sulfonic acid, a m-phenol sulfonic acid, a p-phenol sulfonic acid, and a benzene sulfonic acid; or a naphthalene-α-sulfonic acid. The sulfonic acid based compound includes a mixture of the aliphatic sulfonic acid, the aromatic sulfonic acid, and the naphthalene-α-sulfonic acid.

The process of agitating the mixture of the first glycol based compound, the hydrazide based compound, and the sulfonic acid based compound may be performed for 1 to 60 minutes at a temperature of 20° C. to 200° C. while maintaining the hydrogen ion concentration (pH) of 3 to 5.

The process of performing the fractional distillation of the resultant materials of the agitating includes a first distillation process of removing moisture and low boiling point impurities, and a second distillation process of removing high boiling point formaldehyde.

It can be experimentally confirmed that the second glycol based compound that is recovered through the fractional distillation process has the formaldehyde content of 0 ppm. This will be described in detail with reference to the following examples and comparative examples.

The method for manufacturing a high purity glycol based compound may further include a filtration process of removing fine particles included in the second glycol based compound.

EXAMPLE 1

100 g of dipropylene glycol methyl ether (DPM), 50 ppm of formaldehyde, 0.01 g of succinic acid dihydrazide (SDH), and p-toluene sulfonic acid (TSA) were put in a flask provided with an agitator, and were agitated for 5 minutes at 50° C. while maintaining the hydrogen ion concentration (pH) of 3 to 5. The resultant material of the agitating was put in a round flask of 1000 mL, was distilled through heating using a heater, and then was fractionally distilled using a distillation column which has an inner diameter of 30 mm and which is mounted with a 30-stage sieve tray. A low boiling point impurity, such as a small amount of moisture, was removed through a first distillation column, and the material on a lower portion of the first distillation column was supplied to a secondary distillation column so as to remove a high boiling point formaldehyde to recover a second glycol based compound having a formaldehyde content of 0 ppm. Thereafter, a high purity glycol based organic solvent was recovered through a filtration process of removing fine particles included in the second glycol based compound.

EXAMPLE 2

A high purity glycol based organic solvent was recovered in the same method as the method according to example 1 except that 100 g of diethylene glycol ethyl ether (EDG), 50 ppm of formaldehyde, 0.03 g of adipic acid dihydrazide (ADH), and p-toluene sulfonic acid (TSA) were put in a flask provided with an agitator, and were agitated for 30 minutes at 100° C. while maintaining the hydrogen ion concentration (pH) of 3 to 5.

EXAMPLE 3

A high purity glycol based organic solvent was recovered in the same method as the method according to example 1 except that 100 g of diethylene glycol butyl ether (BDG), 50 ppm of formaldehyde, 0.1 g of propion acid dihydrazide (PPH), and xylene sulfonic acid (XSA) were put in a flask provided with an agitator, and were agitated for 60 minutes at 30° C. while maintaining the hydrogen ion concentration (pH) of 3 to 5.

EXAMPLE 4

A high purity glycol based organic solvent was recovered in the same method as the method according to example 1 except that 100 g of diethylene glycol butyl ether (BDG), 50 ppm of formaldehyde, 0.03 g of benzyl hydrazide (BzH), and xylene sulfonic acid (XSA) were put in a flask provided with an agitator, and were agitated for 30 minutes at 70° C. while maintaining the hydrogen ion concentration (pH) of 3 to 5.

EXAMPLE 5

A high purity glycol based organic solvent was recovered in the same method as the method according to example 1 except that 100 g of ethylene glycol propyl ether (EGPE), 50 ppm of formaldehyde, 0.07 g of octanoate hydrazide (ONH), and p-toluene sulfonic acid (TSA) were put in a flask provided with an agitator, and were agitated for 20 minutes at 50° C. while maintaining the hydrogen ion concentration (pH) of 3 to 5.

EXAMPLE 6

A high purity glycol based organic solvent was recovered in the same method as the method according to example 1 except that 100 g of diethylene glycol ethyl ether (EDG), 50 ppm of formaldehyde, 0.05 g of succinic acid dihydrazide (SDH), and p-toluene sulfonic acid (TSA) were put in a flask provided with an agitator, and were agitated for 2 minutes at 100° C. while maintaining the hydrogen ion concentration (pH) of 3 to 5.

EXAMPLE 7

A high purity glycol based organic solvent was recovered in the same method as the method according to example 1 except that 100 g of ethylene glycol propyl ether (EGPE), 50 ppm of formaldehyde, 0.07 g of adipic acid dihydrazide (ADH), and xylene sulfonic acid (XSA) were put in a flask provided with an agitator, and were agitated for 10 minutes at 150° C. while maintaining the hydrogen ion concentration (pH) of 3 to 5.

COMPARATIVE EXAMPLE 1

A high purity glycol based organic solvent was recovered in the same method as the method according to example 1 except that 100 g of diethylene glycol butyl ether (BDG), 50 ppm of formaldehyde, 0.1 g of sodium sulfite, and p-toluene sulfonic acid (TSA) were put in a flask provided with an agitator, and were agitated for 30 minutes at 70° C. while maintaining the hydrogen ion concentration (pH) of 3 to 5.

COMPARATIVE EXAMPLE 2

A high purity glycol based organic solvent was recovered in the same method as the method according to example 1 except that 100 g of diethylene glycol ethyl ether (EDG), 50 ppm of formaldehyde, 0.1 g of ammonia, and xylene sulfonic acid (XSA) were put in a flask provided with an agitator, and were agitated for 60 minutes at 50° C. while maintaining the hydrogen ion concentration (pH) of 3 to 5.

COMPARATIVE EXAMPLE 3

A high purity glycol based organic solvent was recovered in the same method as the method according to example 1 except that 100 g of dipropylene glycol methyl ether (DPM), 50 ppm of formaldehyde, 0.1 g of dinitrophenyl hydrazine (DNPH), and p-toluene sulfonic acid (TSA) were put in a flask provided with an agitator, and were agitated for 50 minutes at 100° C. while maintaining the hydrogen ion concentration (pH) of 3 to 5.

COMPARATIVE EXAMPLE 4

A high purity glycol based organic solvent was recovered in the same method as the method according to example 1 except that 100 g of dipropylene glycol methyl ether (DPM), 50 ppm of formaldehyde, and 0.07 g of adipic acid hydrazide (ADH) were put in a flask provided with an agitator, and were agitated for 60 minutes at 50° C.

COMPARATIVE EXAMPLE 5

A high purity glycol based organic solvent was recovered in the same method as the method according to example 1 except that 100 g of diethylene glycol butyl ether (BDG), 50 ppm of formaldehyde, and 0.05 g of succinic acid dihydrazide (SDH) were put in a flask provided with an agitator, and were agitated for 2 minutes at 100° C.

COMPARATIVE EXAMPLE 6

A high purity glycol based organic solvent was recovered in the same method as the method according to example 1 except that 100 g of diethylene glycol ethyl ether (EDG), 50 ppm of formaldehyde, and 0.03 g of adipic acid dihydrazide (ADH) were put in a flask provided with an agitator, and were agitated for 30 minutes at 100° C.

COMPARATIVE EXAMPLE 7

A high purity glycol based organic solvent was recovered in the same method as the method according to example 1 except that 100 g of dipropylene glycol methyl ether (DPM), 50 ppm of formaldehyde, and 0.05 g of adipic acid hydrazide (ADH) were put in a flask provided with an agitator, and were agitated for 10 minutes at 70° C.

COMPARATIVE EXAMPLE 8

A high purity glycol based organic solvent was recovered in the same method as the method according to example 1 except that 100 g of diethylene glycol ethyl ether (EDG) and 50 ppm of formaldehyde were put in a flask provided with an agitator, and were agitated for 30 minutes at 50° C.

COMPARATIVE EXAMPLE 9

A high purity glycol based organic solvent was recovered in the same method as the method according to example 1 except that 100 g of diethylene glycol ethyl ether (EDG), 50 ppm of formaldehyde, and 1 g of activated carbon were put in a flask provided with an agitator, and were agitated for 10 minutes at 100° C.

COMPARATIVE EXAMPLE 10

A high purity glycol based organic solvent was recovered in the same method as the method according to example 1 except that 100 g of ethylene glycol propyl ether (EGPE), 50 ppm of formaldehyde, and 5 g of activated carbon were put in a flask provided with an agitator, and were agitated for 60 minutes at 50° C.

Compositions according to examples 1 to 7 and comparative examples 1 to 10 are summarized as in Table 1 below.

TABLE 1

|  | Organic solvent | Formaldehyde input | Formaldehyde remover (Addition amount) | Acid catalyst | Active carbon addition amount | Agitating temp. | Agitating time |
| --- | --- | --- | --- | --- | --- | --- | --- |
| Ex. 1 | DPM | 50 ppm | SDH (0.01 g) | TSA | — | 50° C. | 5 min |
| Ex. 2 | EDG | 50 ppm | ADH (0.03 g) | TSA | — | 100° C. | 30 min |
| Ex. 3 | BDG | 50 ppm | PPH (0.1 g) | XSA | — | 30° C. | 60 min |
| Ex. 4 | BDG | 50 ppm | BzH (0.03 g) | XSA | — | 70° C. | 30 min |
| Ex. 5 | EGPE | 50 ppm | ONH (0.07 g) | TSA | — | 50° C. | 20 min |
| Ex. 6 | EDG | 50 ppm | SDH (0.05 g) | TSA | — | 100° C. | 2 min |
| Ex. 7 | EGPE | 50 ppm | ADH (0.07 g) | XSA | — | 150° C. | 10 min |
| Com. Ex. 1 | BDG | 50 ppm | Sodium sulfite (0.1 g) | TSA | — | 70° C. | 30 min |
| Com. Ex. 2 | EDG | 50 ppm | Ammonia (0.1 g) | XSA | — | 50° C. | 60 min |
| Com. Ex. 3 | DPM | 50 ppm | DNPH (0.1 g) | TSA | — | 100° C. | 30 min |
| Com. Ex. 4 | DPM | 50 ppm | ADH (0.07 g) | — | — | 50° C. | 60 min |
| Com. Ex. 5 | BDG | 50 ppm | SDH (0.05 g) | — | — | 100° C. | 2 min |
| Com. Ex. 6 | EDG | 50 ppm | ADH (0.03 g) | — | — | 100° C. | 30 min |
| Com. Ex. 7 | DPM | 50 ppm | ADH (0.05 g) | — | — | 70° C. | 10 min |
| Com. Ex. 8 | EDG | 50 ppm | — | — | — | 50° C. | 30 min |
| Com. Ex. 9 | EDG | 50 ppm | — | — | 1 g | 100° C. | 10 min |
| Com. Ex. 10 | EGPE | 50 ppm | — | — | 5 g | 50° C. | 60 min |

TABLE 2

|  | Formaldehyde content |
| --- | --- |
| Example 1 | 0 ppm |
| Example 2 | 0 ppm |
| Example 3 | 0 ppm |
| Example 4 | 0 ppm |
| Example 5 | 0 ppm |
| Example 6 | 0 ppm |
| Example 7 | 0 ppm |
| Comparative example 1 | 30 ppm |
| Comparative example 2 | 24 ppm |
| Comparative example 3 | 15 ppm |
| Comparative example 4 | 12 ppm |
| Comparative example 5 | 9 ppm |
| Comparative example 6 | 9 ppm |
| Comparative example 7 | 13 ppm |
| Comparative example 8 | 41 ppm |
| Comparative example 9 | 33 ppm |
| Comparative example 10 | 32 ppm |

Referring to Table 2, the formaldehyde content was 0 ppm according to the examples 1 to 7 of the present invention,

EXPERIMENTAL EXAMPLE 1

Using a gas chromatography method, purities according to examples 1 to 7 and comparative examples 1 to 10 were analyzed, and formaldehyde content in glycol based organic solvent was quantized using US EPA 8315A analyzing method. The results are as shown in Table 2 below.

whereas formaldehyde of minimum 9 ppm to maximum 41 ppm was detected according to the comparative examples 1 to 10.

While the present invention has been particularly shown and described with reference to exemplary embodiments and examples thereof, it will be understood by those of ordinary skill in the art that various changes in form and detail may be made therein without departing from the spirit and scope of the present invention as defined by the following claims.

The exemplary embodiments should be considered in a descriptive sense only and not for purposes of limitation.

What is claimed is:

1. A method for manufacturing a formaldehyde free glycol based compound, comprising:
   agitating a mixture of a first glycol based compound, a formaldehyde, a hydrazide based compound, and a sulfonic acid based compound; and
   performing fractional distillation of resultant materials of the agitating to recover a second glycol based compound having a formaldehyde content of 0 ppm.

2. The method of claim 1, wherein the agitating the mixture of the first glycol based compound, the hydrazide based compound, and the sulfonic acid based compound is performed for 1 to 60 minutes at a temperature of 20° C. to 200° C. while maintaining a hydrogen ion concentration (pH) of 3 to 5.

3. The method of claim 2, wherein the performing the fractional distillation of the resultant materials of the agitating comprises a first distillation process of removing moisture and low boiling point impurities, and a second distillation process of removing high boiling point formaldehyde.

4. The method of claim 2, further comprising performing a filtration process of removing fine particles comprised in the second glycol based compound.

5. The method of claim 2, wherein the first glycol based compound is at least one selected from the group consisting of $C_1$ to $C_6$ alkylene glycols, $C_1$ to $C_6$ alkyl ether based compounds of $C_1$ to $C_6$ alkylene glycols, and $C_1$ to $C_6$ alkyl ether acetate based compounds of $C_1$ to $C_6$ alkylene glycols.

6. The method of claim 5, wherein the first glycol based compound is at least one selected from the group consisting of ethylene glycol, propylene glycol, butylenes glycol, ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether, diethylene monoglycol methyl ether, diethylene monoglycol ethyl ether, diethyleneglycol diethyl ether, diethylene glycol monobutylenes ether, diethyleneglycol dibutyl ether, dipropyleneglycol monomethyl ether, dipropyleneglycol dimethyl ether, dipropyleneglycol monobuty ether, dipropyleneglycol dibutyl ether, triethylene glycol monomethyl ether, triethylene glycol dimethyl ether, triethylene glycol monoethyl ether, triethylene glycol diethyl ether, triethyleneglycol monobutyl ether, and triethyleneglycol dibutyl ether, ethylene glycol methyl ether acetate, ethylene glycol monoethyl ether acetate, ethylene glycol monobutyl ether acetate, and propylene glycol monomethyl ether acetate.

7. The method of claim 1, wherein the hydrazide based compound is at least one selected from the group consisting of acetic hydrazide, octanoate hydrazide, succinic acid dihydrazide, propionic acid hydrazide, benzyl hydrazide, oxalic acid dihydrazide, malic acid dihydrazide, glutaric acid dihydrazide, adipic acid dihydrazide, sebacic acid dihydrazide, maleic dihydrazide, fumaric acide dihydrazide, itaconic acide dihydrazide, carbonic acid dihydrazide, phthalic acid dihydrazide, terephthalic acid dihydrazide, isophtalic acid dihydrazide, 1,2,4-butane tri carbohydrazide, 1,1,4-butane tri carbohydrazide, 1,2,5-pentane tri carbohydrazide, 1,3,6-hexane tri carbohydrazide, 1,3,7-heptane tri carbohydrazide, 1-hydroxy-1,2,4-butane tri carbohydrazide, 3-bromobenzoic acid hydrazide, 4-bromobenzoic acid hydrazide, 2-chlorobenzoic acid hydrazide, 4-chlorobenzoic acid hydrazide, 2-fluorobenzoic acid hydrazide, 3-fluorobenzoic acid hydrazide, 4-fluorobenzoic acid hydrazide, 3-hydroxybenzoic acid hydrazide, salicylic acid hydrazide, 2,4-dihydroxybenzoic acid hydrazide, 2-aminobenzoic acid hydrazide, 4-aminobenzoic acid hydrazide, 2,4-diaminobenzoic acid hydrazide, paratoluic hydrazide, phenylacetic hydrazide, 4-methoxy-benz hydrazide, and 2-hydroxy-4-methoxy benzoic acid hydrazide.

8. The method of claim 7, wherein the hydrazide based compound is added to the first glycol based compound with a content of 0.005 to 1.0 parts by weight with respect to 100 parts by weight of the first glycol based compound.

9. The method of claim 1, wherein the sulfonic acid based compound is at least one selected from the group consisting of an aliphatic sulfonic acid comprising a methane sulfonic acid and an ethane sulfonic acid; an aromatic sulfonic acid comprising an o-toluene sulfonic acid, a m-toluene sulfonic acid, a p-toluene sulfonic acid, an o-phenol sulfonic acid, a m-phenol sulfonic acid, a p-phenol sulfonic acid, and a benzene sulfonic acid; and a naphthalene-α-sulfonic acid.

* * * * *